United States Patent
Krivacic et al.

(10) Patent No.: US 7,545,498 B2
(45) Date of Patent: Jun. 9, 2009

(54) SYSTEM AND METHOD FOR REMOVING AUTO-FLUORESCENCE THROUGH THE USE OF MULTIPLE DETECTION CHANNELS

(75) Inventors: Robert T. Krivacic, San Jose, CA (US); Huangpin B. Hsieh, Mountain View, CA (US); Douglas N. Curry, Menlo Park, CA (US); Richard H. Bruce, Los Altos, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 172 days.

(21) Appl. No.: 11/612,228

(22) Filed: Dec. 18, 2006

(65) Prior Publication Data

US 2008/0144009 A1 Jun. 19, 2008

(51) Int. Cl.
*G01N 21/64* (2006.01)
(52) U.S. Cl. .................................... 356/417; 250/461.2
(58) Field of Classification Search ................. 356/318, 356/417; 250/461.2
See application file for complete search history.

(56) References Cited

U.S. PATENT DOCUMENTS

| | | | |
|---|---|---|---|
| 5,480,804 A * | 1/1996 | Niwa et al. | ............. 435/286.1 |
| 7,113,624 B2 | 9/2006 | Curry | |
| 7,277,569 B2 | 10/2007 | Bruce et al. | |
| 2005/0138152 A1 | 6/2005 | Kruse | |
| 2006/0132778 A1 | 6/2006 | Curry et al. | |
| 2006/0132878 A1 | 6/2006 | Curry et al. | |

FOREIGN PATENT DOCUMENTS

| | | |
|---|---|---|
| EP | 1 672 355 A | 6/2006 |
| JP | 08 334466 A | 12/1996 |

OTHER PUBLICATIONS

European Search Report, App. No. EP 07 12 3123, Dated Apr. 14, 2008, Examiner William Mason.
Keller, P. et al., "Photodynamic Imaging of a Rat Pancreatic Cancer with Pheophorbide A", *Photochemistry and Photobiology*, Oxford, GB, vol. 63, No. 6, 1996, pp. 860-867.
Andersson-Engels, S. et al., "Medical Diagnostic System Based on Simultaneous Multispectral Fluorescence Imaging", *Applied Optics*, OSA, Optical Society of America, Washington, DC, US, vol. 33, No. 34, Dec. 1, 1994, pp. 8022-8029.

(Continued)

*Primary Examiner*—F. L Evans
(74) *Attorney, Agent, or Firm*—Fay Sharpe LLP (57) ABSTRACT

A system and method permits for the separation of auto-fluorescence from a signal by applying a single probe to a sample, exciting the sample with a single wavelength light source, thereby emitting a light a distance from the light source. The emitted light is split, and the split light is collected into two or more distinct channels. A first channel of the distinct channels is positioned closer to the light source than a second distinct channel of the distinct channels, and the second channel is closer to the emission frequency of the single probe than is the first channel. The light collected in the first channel and the light collected in the second channel are investigated, and an output signal is generated based upon the investigation.

21 Claims, 5 Drawing Sheets

OTHER PUBLICATIONS

Andersson, P. S. et al., "Multispectral System for Medical Fluorescence Imaging", *IEEE Journal of Quantum Electronics USA*, vol. QE-23, No. 10, Oct. 1987, pp. 1798-1805.

Wan Wade, K. et al., "Measurement of Drub Distribution in Vascular Tissue Using Quantitative Fluorescence Microscopy", *Journal of Pharmaceutical Sciences, American Pharmaceutical Assoc.*, Washington, US, vol. 88, No. 8, Aug. 1999, pp. 822-829.

Tassetti, V., et al., "In Vivo Laser-Induced Fluorescence Imaging of a Rat Pancreatic Cancer with Pheophorbide A", *Photochemistry and Photobiology*, Oxford, GB, vol. 65, No. 6, 1997, pp. 997-1006.

* cited by examiner

SYSTEM AND METHOD FOR REMOVING AUTO-FLUORESCENCE THROUGH THE USE OF MULTIPLE DETECTION CHANNELS

BACKGROUND

The present exemplary embodiments relate to the imaging arts and find particular application in conjunction with low and high-density cell detection, locating, and identifying in blood smears, biological assays, and the like across distinct imaging systems, and will be described with particular reference thereto. However, it is to be appreciated the exemplary embodiments will also find application in imaging, locating and identifying other types of low- or high-density features on various substantially planar surfaces and samples, such as imaging semiconductor wafers, imaging particulate contaminants in fluids or thin solid films, and so forth, with such imaging finding specific uses in the printing arts, electronic arts, medical arts, and other scientific and engineering areas.

In rare cell studies, a particular problem arises due to the typically low concentration of the rare cells in the blood or other body fluid. In a typical rare cell study, blood is processed to remove cells that are not needed. Then a probe, such as a fluorescent material, is applied that attaches to antibodies, which in turn selectively attach to a cell surface or cellular protein of the rare cells. The cellular proteins may be membrane proteins or proteins within a cell, such as cytoplasm proteins. The antibodies may also attach to other types of molecules of the rare cell, as well as to DNA.

The fluorescent material may be a fluorescent marker dye or any other suitable material which will identify the cells of interest. A smear treated in this manner, which may include the blood and/or components of the blood, is prepared and optically analyzed to identify rare cells of the targeted type. For statistical accuracy it is important to obtain as large a number of cells as required for a particular process, in some studies at least ten rare cells should be identified, requiring a sampling of at least ten million cells, for a one-in-one-million rare cell concentration. Such a blood smear typically occupies an area of about 100 cm$^2$. It is to be understood, however, that this is simply one example and other numbers of cells may be required for statistical accuracy for a particular test or study. Other cell identifiers which are being used and investigated are quantum dots and nano-particle probes. Also, while a rare cell is mentioned as a one-in-one-million cell concentration, this is not intended to be limiting and is only given as an example of the rarity of the cells being sought. The concepts discussed herein are to be understood to be useful in higher or lower levels of cell concentration.

The ability to scan large numbers of cells at a high rate is considered a key aspect which increases the throughput of testing processes. Therefore, it is considered valuable to provide a system which improves the speed, reliability and processing costs which may be achieved by cell detection systems and/or processes.

Fiber array scanning technology (FAST) provide particular systems and processes that increase the speed at which scanning of a sample and the detection of potential or candidate rare cells may be accomplished, and therefore lends itself to the investigation of large samples.

In general, in FAST systems, a sample of material to be examined is treated with fluorescent material (e.g., a selectively attaching or labeling dye), typically by introducing a measured amount of the material into the sample itself. The sample is applied to a slide, and radiation, typically laser light, is scanned across the sample. This provides essentially a raster scanning of the sample, with the position of incidence of the laser on the sample, usually relative to a fiducial mark on the slide, precisely known at all times. The output intensity of the light resulting from the scanned laser beam varies with position on the surface of the sample. Appropriate hardware detects selected wavelengths of the output light, and a processor analyzes the detected output light and associates fluorescence events and locations.

In FAST systems, and most other detection systems, it is important to be able to rule out as many false positives (i.e., incorrect identification of a target cell) as possible. One source of such false positives is dust, debris, healthy cells, etc., which emit light in response to the incident input light even without the attachment of fluorescent dye (referred to herein as auto-fluorescence). In order to identify auto-fluorescence events, and thus enable ruling out such false positives, when a single dye is employed, it is typical to use a large enough quantity of dye in the sample so fluorescence events are much brighter than the auto-fluorescence events. However, the dye used is relatively expensive, and when too much dye is used, it loses its ability to selectively attach to the target cells, instead saturating the sample and attaching to a variety of unintended components in the sample.

In another approach to reducing false positives due to auto-fluorescence, two different dye materials are introduced into the sample, each dye material fluorescing at a different wavelength in response to incident radiation. Each dye attaches relatively equally to the target cells. Since auto-fluorescence events are brightest closer to the input wavelength, one of the dyes is chosen such that its fluorescence wavelength is relatively far from the source wavelength. Fluorescence events are examined at the output wavelengths of both dyes. Fluorescence events predominantly at only one of the wavelengths are considered to be false positives, such as would arise form auto-fluorescence, while events emitting at both wavelengths are considered to be indicative of the presence of a target cell.

This dual-dye arrangement has the disadvantage that significant amounts of dye need to be introduced into the sample. In addition, in certain instances, the ratio of one "color" of dye to the other must be carefully controlled. For example, when scanning with a 488 nm laser and sampling with "green" and "red" dyes (i.e., dyes that fluoresce in the green and red wavelength bands, respectively), the light emitted due to auto-fluorescence is greater in the green channel than in the red channel. This requires balancing the ratio of the two dyes such that fluorescent emission caused by the incident laser light is stronger in the red than in the green portions of the spectrum. Excitation is significantly less efficient for the red dye than for the green dye. Thus, significantly more red dye must be introduced into the sample. Ratios of 33:1 red to green are typical. The aforementioned cost and saturation problems, as well as cross-talk and interference between the fluorescing, can therefore arise.

To overcome issues related to the use of two different dyes, U.S. Ser. No. 11/018,759 provides a technique for alternative scanning of two separate laser beams in an attempt to minimize cross-talk and interference between the fluorescence which occurs through the use of two different probes emitting at different wavelengths. However, this technique has its own drawbacks, including the previously mentioned expense and complication of sample preparation and data analysis. Particularly, and as previously mentioned, because the excitation of a first probe, for example, a red dye may be less efficient than a second probe, for example, a green dye, about 33 times more red dye must be used than green dye. This requirement makes the processing of samples more complex and increases overall expense. Further, the use of high amounts of red dye or other probe materials may, again, cause accumulations or aggregation of the dye or materials, which is undesirable.

Therefore, there is a need in the art for a process and system for scanning for rare cells using a single laser with reduced cost and complexity, such as requiring only a single dye, yet is capable of ruling out false positives such as those occurring due to auto-fluorescence events.

INCORPORATION BY REFERENCE

The following co-pending applications U.S. Ser. No. 10/271,347, filed Oct. 15, 2002 (now U.S. Pat. No. 7,113,624), entitled, "Imaging Apparatus And Method Employing A Large Linear Aperture", by Douglas N. Curry; Ser. No. 10/616,366, filed Jul. 9, 2003, entitled, "Apparatus And Method For Detecting And Locating Rare Cells", by Richard H. Bruce, et al.; U.S. Ser. No. 11/018,759, filed Dec. 21, 2004, entitled, "Time-Multiplexed Scanning Light Source For Multi-Probe, Multi-Laser Fluorescence Detection Systems", by Douglas N. Curry, et al.; and U.S. Ser. No. 10/740,974, Dec. 19, 2003, entitled, "Method Of Converting Rare Cell Scanner Image Coordinates To Microscope Coordinates Using Reticle Marks On A Sample Media", by Douglas N. Curry, et al., are hereby incorporated by reference in their entirety.

BRIEF DESCRIPTION

A system and method permits for the separation of auto-fluorescence from a signal by applying a single probe to a sample, exciting the sample with a single wavelength light source, thereby emitting a light a distance from the light source. The emitted light is split, and the split light is collected into two or more distinct channels. A first channel of the distinct channels is positioned closer to the light source than a second distinct channel of the distinct channels, and the second channel is closer to the emission frequency of the single probe than is the first channel. The light collected in the first channel and the light collected in the second channel are investigated, and the results are based upon the investigation.

BRIEF DESCRIPTION OF THE DRAWINGS

The embodiments may take form in various components and arrangements of components, and in various steps and arrangements of steps. The drawings are only for purposes of illustrating preferred embodiments and are not to be construed as limiting the application.

DETAILED DESCRIPTION

Figure 1:
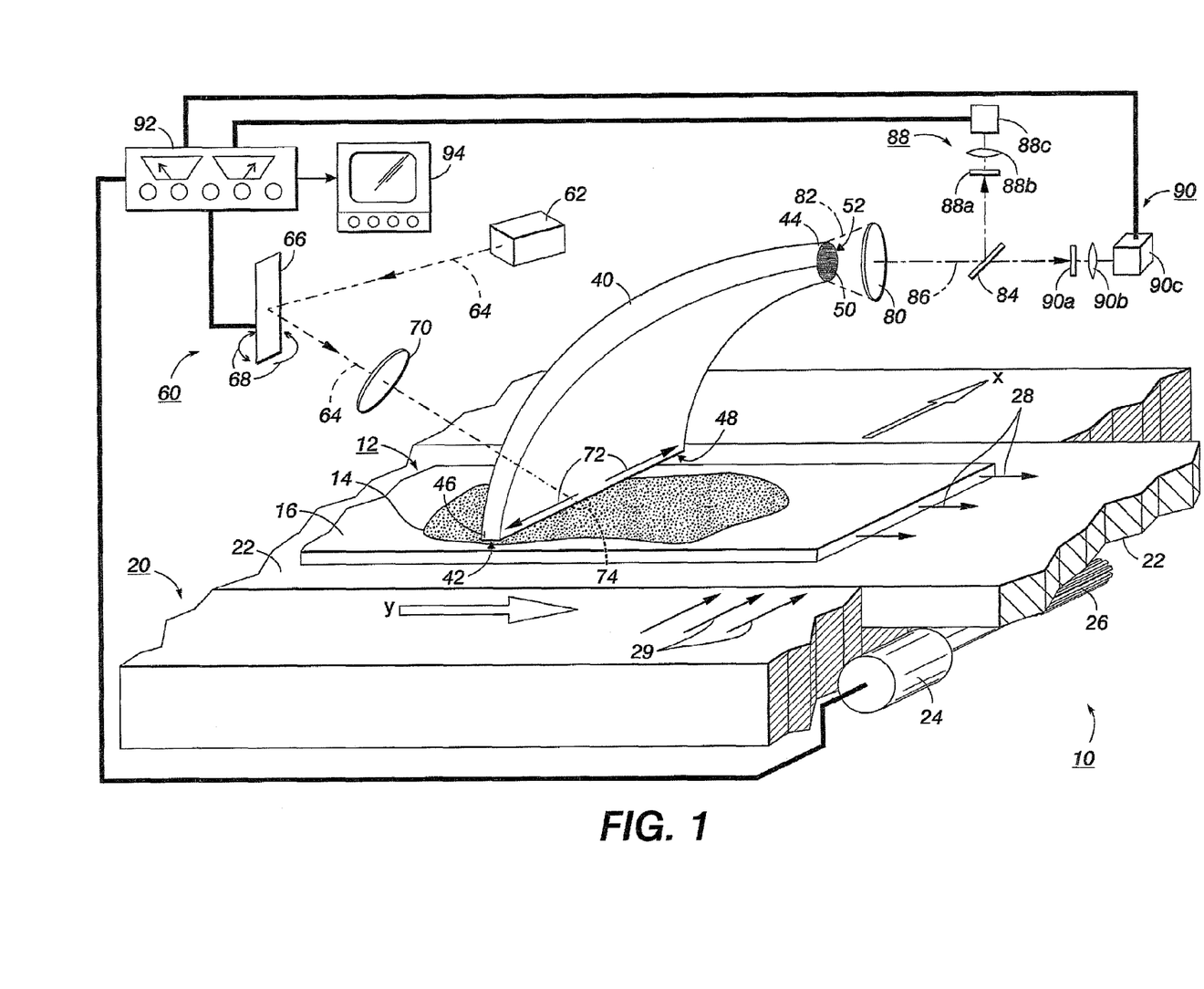
FIG. 1 shows a perspective view of an imaging apparatus suitable for incorporating features of a preferred embodiment.

With reference to FIG. 1, an imaging apparatus is described which utilizes a galvanometer-based laser scanning system employing a single laser transmitter and a two-channel detector arrangement. In the figure, imaging apparatus or imager 10 examines a sample 12 such as a biological smear 14 disposed on at least a portion of a surface of a slide 16. Imaging apparatus or imager 10, as expanded upon below, is designed for detection of minute or microscopic material.

As is known in the art, for cell studies sample 12 is suitably prepared by drawing a sample of a biological fluid such as, but not limited to, blood or parts of blood from a subject. In a preferred embodiment, the sample is a monolayer of cells. The fluid sample is treated with a probe, such as but not limited to a marker dye that selectively bonds to different kinds of biological molecules, which may be on the surface or inside the cell, such as proteins, nucleic acids or other molecules. Suitable markers are known in the art for marking a number of different cell types of clinical interest, including selected cancer cell types, fetal cells, or other appropriate cells to be considered. Work is also being undertaken to develop marking materials for numerous other cells such as brain cells, liver cells, as well as bacteria cells, among others. The material preferably emits a characteristic output, such as fluorescence or phosphorescence, responsive to a selected excitation irradiation, such as irradiation by a selected wavelength or spectrum of light, x-ray irradiation, electron-beam irradiation, or the like. The characteristic luminescence typically has a characteristic wavelength or spectral range of wavelengths. While dyes are the predominant tagging process, other techniques exist including the use of markers known as quantum dots and DNA nano-particle probes.

The sample 12, including a single marker or probe, is mounted on an imager translation stage, or slide holder, 20 (shown in part) which includes a linearly translatable track 22 that supports the sample 12. A motor 24 connects with the track 22 via gearing 26 to translate the track 22 and the supported sample 12 along a y-direction (indicated by arrows 28) and a x-direction (indicated by arrows 29). Although translation stage 20 driven by a rotary motor 24 is shown in FIG. 1, it is also contemplated to employ other types of mechanical driving devices. Furthermore, other types of sample movement such as sample rotation are also contemplated.

A fiber optic bundle 40 includes a first end 42 that is proximate to the sample 12, and a second end 44 that is distal from the sample 12. The first end 42 includes a plurality of first fiber ends 46 arranged substantially parallel to one another in an arrangement that defines a generally linear or high-aspect-ratio rectangular input aperture 48 with a long dimension aligned with the x-direction. The input aperture 48 preferably includes a large number of first fiber ends 46, i.e. thousands of fiber ends. In one suitable embodiment, 40,000 fibers each having an approximately 50 micron diameter are arranged into a 40 fiber-by-1000 fiber array to define the input aperture 48 with a long dimension of approximately 5 cm and a short dimension of about 0.2 cm corresponding to a 25:1 aspect ratio. The first fiber ends 46 can be arranged in a regular pattern. Alternatively, the first fiber ends can be arranged in an irregular or non-periodic array and may have diameters which are greater or less than 50 microns. Although generally round, the fiber ends may also be oval, square, hexagonal, or of other cross-sectional shapes. The first fiber ends 46 are oriented substantially perpendicular to the plane of the biological smear 14 so as to view smear 14.

The optical fiber bundle 40 "morphs" or changes cross-sectional dimensions and shape between the first end 42 to the second end 44 such that the second end 44 includes a plurality of second fiber ends 50 that define a compact, generally circular output aperture 52. Preferably, there is a one-to-one correspondence between the first fiber ends 46 and the second fiber ends 50, and each first fiber end connects with a second fiber end by an individual, distinct fiber having its own waveguiding cladding. Alternatively, each fiber can include only a light-transmissive fiber core, and an ambient/core interface functions to waveguide the light. Other optical fiber types can also be used, such fibers being well known in the art and typically formed of glass, plastic, or other light-transmissive materials by extrusion methods. The morphed shape of the fiber bundle 40 from an extended, generally linear first end 42 to a compact, generally circular second end 44 is preferably formed by varying a spatial arrangement of the fibers of the optical fiber bundle 40 in a continuous fashion. For the exemplary 40,000 fiber embodiment with each fiber having a 50 micron diameter, the generally circular output aperture 52 has a circular diameter of about 1.3 cm.

Although for convenience in arranging the fibers it is contemplated to arrange the first and second fiber ends 46, 50 in the respective apertures 48, 52 with a selected correspondence relative to one another, the fiber ends 46, 50 can instead have a generally uncorrelated and arbitrary relationship therebetween. Morphed fiber optic bundles similar to the fiber optic bundle 40 are known and used in the optical arts for other applications such as transforming focused light into a linear illumination pattern, and for coupling a light beam into a linear slit of a monochromator or spectrometer.

To obtain good light transmission, the fiber optic bundle 40 preferably has a high fiber packing factor, for example, fiber optic bundle 40 has a packing factor of about 0.80 or higher. Other factors influencing the light transmission include the polishing or light transmission properties of the tips of the first and second fiber ends 46, 50, the absorption per unit length of the fibers, and the overall length of the fibers. Bending losses are preferably reduced by avoiding sharp bends of the fiber optic bundle 40.

It is understood that while a fiber bundle has been described as the mode of transport of the acquired light, other existing or subsequently developed light transmission component or light path or pipe which includes the appropriate characteristics may be employed as the light path or light pipe.

With continuing reference to FIG. 1, a scanning radiation (light) source 60 in a suitable embodiment includes a laser 62 that produces excitation light (radiation beam) 64 at a wavelength or wavelength range selected to excite the material used in marking the biological smear 14. The excitation light 64 is angularly scanned by a galvanometer 66 that has a reflective surface that rotates (indicated by curved arrows 68) responsive to an electrical input. An optional focusing lens 70 focuses the angularly scanned excitation light 64 onto the sample 12, and more particularly onto the biological smear 14. The angular scanning produced by the rotating mirror 66 translates into a linear sweeping or fast scanning (indicated by arrows 72) of the excitation light on the biological smear 14 along a linear trajectory 74 arranged below the input aperture 48 and parallel to the long dimension of the input aperture 48. That is, using the coordinate system of FIG. 1 the linear trajectory 74 is parallel to the x-direction. In a suitable embodiment, the trajectory 74 is disposed on the biological smear 14 about one millimeter below the input aperture 48, although other distances will be appropriate dependant upon devices and the environment in which these concepts are implemented.

For cell studies, the excitation radiation 64 preferably produces a spot size on the biological smear 14 which substantially comports with a size of the cells, which may vary in size but are typically about one to thirty microns in size. To obtain such narrow beam focusing, the focusing lens 70 is typically included.

With continuing reference to FIG. 1, an electronic control unit 80 communicates with the galvanometer 66 and the translation stage 20 to coordinate the linear sweeping or scanning 72 of the radiation beam 64 along the trajectory 74 and the linear translation 28 of the sample 12 to effectuate a rastering of the radiation beam 64 across a selected area of the sample which is bounded in the x-direction by the smaller of a span of the trajectory 74 and the long dimension of the input aperture 42. Preferably, the span of the trajectory 74 substantially comports with the long dimension of the input aperture 42.

Excitation radiation beam 64 is incident upon the biological smear 14 at an oblique angle which is larger than a collection angle $\theta$ of the input aperture 42. The collection angle $\theta$ depends upon a short dimension of the input aperture 42, the distance between the input aperture 42 and the biological smear 14, and the light collecting characteristics of the first fiber ends 46. The latter is suitably characterized by a numerical aperture of the fiber ends. As is known in the art, an optical fiber end typically has a large numerical aperture corresponding to a large light collection angle which is particularly advantageous for collecting the typically weak characteristic luminescence of the cells. In a suitable embodiment, the radiation beam 64 impinges upon sample 12 at 30°-90°. When beam 64 impinges upon sample 12 at approximately 90°, a bifurcated light path may be provided wherein light is collected on both sides of the scanning beam. One example of such a bifurcated light path is shown in U.S. patent application Ser. No. 11/017,440, filed Dec. 20, 2004, entitled Improved Method and Apparatus for Scanning and Light Collection for a Rare Cell Detector, by Douglas N. Curry et al., hereby fully incorporated by reference.

Because the incidence angle of the radiation beam 64 is larger than the collection angle $\theta$ of the input aperture 42, specularly reflected radiation is not collected by the input aperture 42. However, the characteristic luminescence produced by the treated cells generally emits uniformly in all spatial directions, i.e. each treated cell corresponds to a point light source. Hence, a substantial portion of the characteristic luminescence is collected by the input aperture 42 due to its close proximity to and alignment with the radiation beam trajectory 74 on the biological smear 14 as well as the large numerical aperture of the first fiber ends 46. The collected light enters the first fiber ends 46, transmits along the individual fibers, and exits the optical fiber bundle 40 at second fiber ends 50 that correspond to the collecting first fiber ends 46.

It will be appreciated that the characteristic luminescence produced by a particular cell will not generally be collected by all or even most of the first fiber ends 46. Rather, only one or a few of the first fiber ends 46 which are closely proximate to the cell will collect the characteristic luminescence therefrom. In an exemplary embodiment, the radiation spot size is about 7-14 microns corresponding to a similarly sized cell (or in other embodiments, between 7-15 microns or other appropriately sized spot), while each first fiber end 46 has a diameter of about 50 microns. Hence, only one or a few fibers may be needed to view and collect the characteristic luminescence for any given position of the sweeping radiation beam 64.

However, because at the second end 44 of the fiber bundle 40 the second fiber ends 50 are arranged to define the compact, output aperture 52, the characteristic luminescence emanates from a small region of space corresponding to the output aperture 52 regardless of which of the first fiber ends 46 collected the characteristic luminescence. As the excitation beam 64 sweeps along its trajectory 74 parallel to and typically below the input aperture 48, the proximate one or few of the first fiber ends 46 collect the characteristic luminescence, which is channeled by the fiber optic bundle 40 to the compact output aperture 52.

In one suitable embodiment of the present application, first lens 80 includes a lens combination, designed using known optical design methods that collimate light beam 82 emanating from output aperture 52 to within a ±10° angular divergence. A beam splitter 84 is used to direct separate portions of the collimated light beam 86 from lens 80 into one of at least two distinct detection channels 88 and 90. Each of the distinct detection channels may incorporate blocking filters 88a, 90a, which are interference filters with reflectance portions coinciding with the wavelength of the radiation beam 64 employed, and transmission portions corresponding with the wavelength of the characteristic luminescence. As is known in the art, optical interference filters have a rejection ratio that is strongly dependent upon the angle of incidence of the light. An exemplary interference filter used in one actually constructed embodiment exhibits a $10^6$:1 or greater rejection ratio for light incident within ±14° of normal incidence.

With continuing reference to FIG. 1, second lenses 88b, 90b focus the collimated collected light onto photodetector arrangements 88c, 90c, by combining the compact output aperture 52 with focusing optics of first detection channel 88 and second detection channel 90. Photodetectors 88c, 90c of each channel may be single photodetectors, which provide signal detection for the spatially distributed linear input aperture 48. Because of the typically low collected characteristic luminescence intensities produced by treated cells, the photodetectors 88c, 90c may be photomultiplier tubes. As is known in the art, photomultiplier tubes provide substantial signal gain through cascade multiplication of electrons in a multi-stage high-voltage cathode. To further improve the signal-to-noise ratio, the optical paths of the detection channels 88, 90 may be enclosed to substantially reduce noise due to stray light. Outputs from detection channels 88 and 90 are then sent to controller 92 which generates images displayed on display 94.

Those skilled in the art can suitably modify detection channels 88, 90 by addition, removal, or substitution of components to adapt it to specific imaging situations. Also, while two detection channels are illustrated systems with more than two channels may be designed. For applications providing alternate signal-to-noise characteristics, a photodiode can be used for the photodetectors 88c, 90c.

Figure 2:
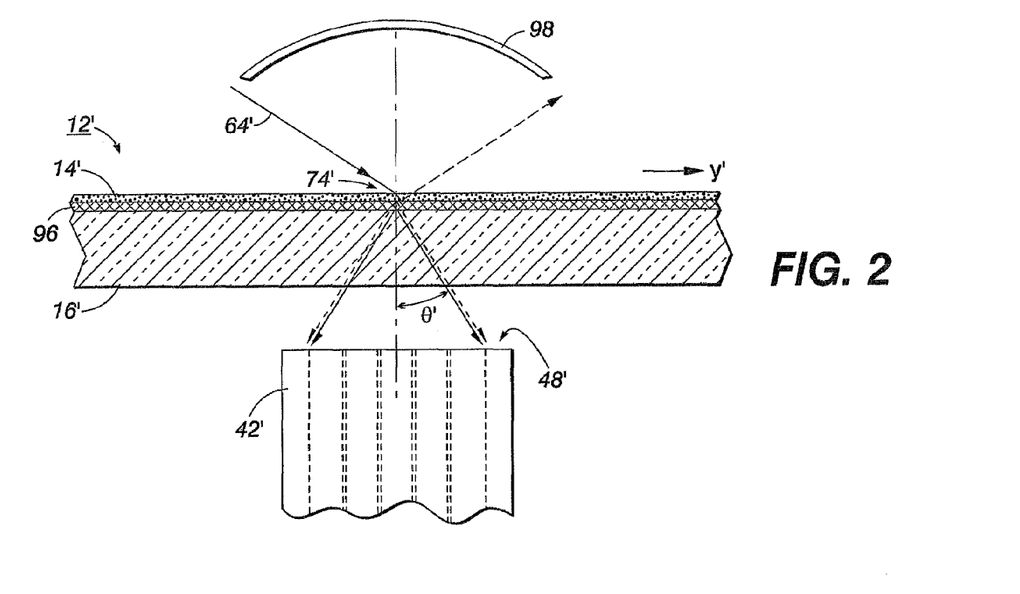
FIG. 2 shows a side view of another embodiment, the view centered on the first end of the morphed fiber optic bundle;.

Although the described embodiments show the stimulated emissions being collected by an aperture 48 arranged above the sample, it is to be appreciated that, as shown in FIG. 2, an input aperture 48' may be arranged to view the sample 12' from below, i.e., from a side of the slide 16' that is opposite the biological smear 14'. That is, the input aperture 48' views the biological smear 14' through the slide 16', which is light transmissive for the characteristic luminescence of the cells. The slide 16' may also include an optional laser blocking filter 96, such as an absorption band pass filter, coating the surface below the biological smear 14'. The embodiment of FIG. 2 may also include an optional cylindrical reflector 98 having a linear focal line generally coinciding with the radiation beam trajectory 74' on the biological smear 14'. The cylindrical reflector 98 can improve the signal to noise ratio for certain imaging applications by increasing the amount of characteristic luminescence that is collected. It will be recognized that the cylindrical reflector 98 can also be used in conjunction with the configuration of FIG. 1.

In the above-described systems, it has been previously considered to be advantageous when scanning fluorescent probes decorating cells to use multiple probes, with each fluorescing at a different wavelength than the other. Examples of such dual probe systems have contemplated use of single and multiple excitation sources.

A problem inherent in the single source excitation approach is that the longer wavelength emission (e.g. of the second probe) is inefficiently stimulated by a single excitation laser and would be more efficiently excited by a laser whose wavelength is closer to its emission. Further, to obtain proper ratios of the emissions from dual probes with one excitation source, the long wavelength emitter is desirably present at a higher concentration in the mixture. Such high concentrations can cause a spread of the ratio of the emissions and can also cause aggregate formation. Since lower concentrations of probes may be used with more efficient excitation, use of multiple excitation sources have been considered.

Figure 3:
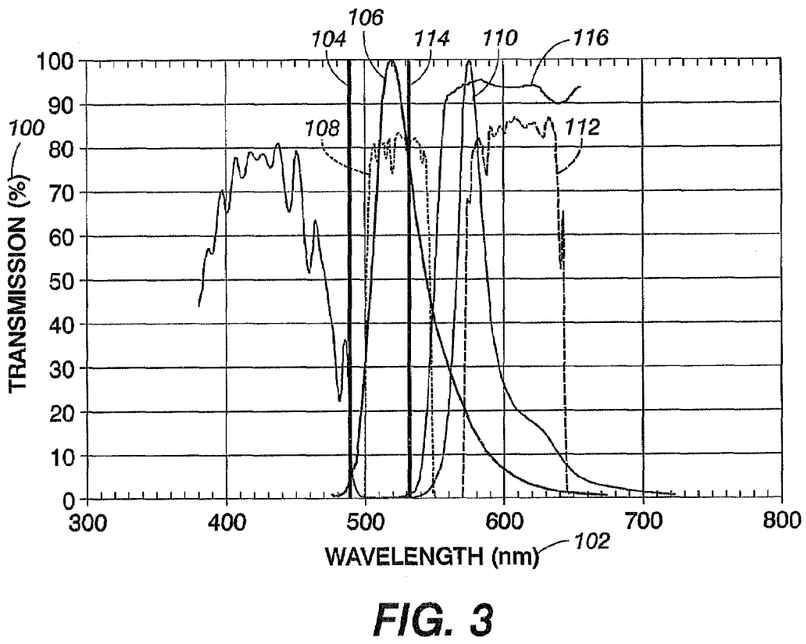
FIG. 3 shows a plot of excitation radiation and resultant stimulated radiation when multiple probes are used.

With reference to FIG. 3, problems associated with the use of dual probes is illustrated. Transmission percentage 100 as a function of wavelength 102 is shown for exemplary wavelengths of interest. A first laser wavelength 104 is shown as a vertical line at 488 nm, which is a suitable laser wavelength for stimulating an FITC probe having a fluorescent emission 106 with peak emission intensity at approximately 520 nm. The difference in wavelength between the laser wavelength 104 and the peak emission wavelength 106 of the FITC probe is known in the art as the Stokes shift. Stokes shift is the difference in wavelength between absorbed and emitted quanta. The emitted wavelength is longer or equal to the incident wavelength due to energy conservation; the difference being absorbed as heat in the atomic lattice of the material. A first emission filter transmission curve 108 is shown which is suitable for filtering any undesirable reflections of the first laser, and other unwanted frequencies, while allowing substantial transmission of the desired probe fluorescence in the range of approximately 505 nm to 545 nm.

If a second R-PE probe 110 having a peak emission intensity at 576 nm is added simultaneously with the first probe 106, it may be observed that several problems arise. The emissions from the second probe overlap significantly with the emissions from the first probe (signal crosstalk) in the range of approximately 550 nm to 600 nm, making it difficult to differentiate between first and second probe emissions. In this exemplary case, a second emission filter 112 can be added with a transmission range from approximately 575 nm to 640 nm which partially alleviates the problem by blocking most of the first probe emissions. However, the same disadvantage still exists because of significant remaining crosstalk, even with the use of emission filters. For example, a significant portion of the first probe 106 emissions extends into the transmission band of the second emission filter 112 transmission curve, thereby reducing the sensitivity and signal-to-noise ration of the system.

The above-described signal loss is made more significant by the fact that only a single laser has been included in the system, and the second probe will not be stimulated as efficiently as the first probe because of the larger wavelength difference between the laser wavelength and the second probe 110. To more efficiently stimulate the second probe, a second laser wavelength 114 emitting with a wavelength of 532 nm has been suggested, emitting simultaneously with the first laser wavelength 104. This, however, gives rise to another problem. With a wavelength of 532 nm, the second laser wavelength 104 falls within the transmission range of the first emission filter 108. Because of this, reflections of the second laser wavelength 114 may be erroneously detected as stimulated emissions from the first probe 106.

Figure 4:
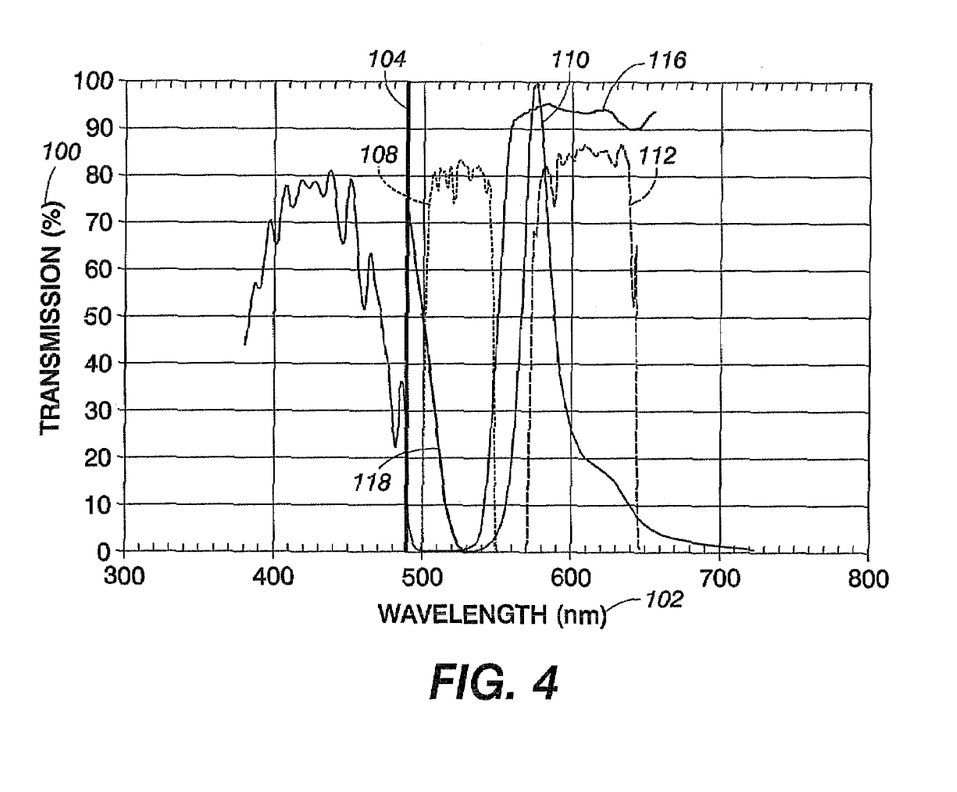
FIG. 4 shows a plot of excitation radiation and resultant stimulated radiation when only a single probe is used.

Turning attention to FIG. 4, illustrated is a plot of excitation radiation and resultant stimulated which more specifically reflects the concepts of the present application.

More particularly, it is known that auto-fluorescence, which occurs in many signal detection systems, including when scanning for rare cells on the FAST system such as shown in FIG. 1, can cause false positives. One technique, as discussed above, to overcome these auto-fluorescence false positives is to use two different probes emitting at different wavelengths, and verify that signals for the probes are in both channels of the system. Such a solution, however, can be expensive, time consuming, and complicate sample preparation and data analysis, if, for no other reason, because the excitation of a red dye type probe, often employed, is less efficient than that of a green dye type probe. Commonly about 33 times more red dye must be used than the green dye in the dual probe-type systems. This again makes the processing complex and expensive. Therefore to simplify the processing steps, and to reduce processing costs and errors, the present concepts, as illustrated by FIG. 4, employs only a single probe 110, and it is further proposed to employ only a single excitation source frequency 104 to produce a detection signal intended for a second input or detection channel (e.g., a red channel or filter) 112. However, the system also includes a first input or detection channel (e.g., a green channel or filter) 108 closer to the excitation frequency of the light source (i.e., the laser) than the emission frequency of the single probe. The concepts of the present embodiments improve detection by taking advantage of auto-fluorescence signals 118 generated in the first channel 108, which will be larger than corresponding auto-fluorescence signals in the second channel 112, since the first channel is located closer to the excitation frequency of the excitation source (e.g., the laser) and the frequency of the auto-fluorescence signals are closer to the excitation frequency of the laser than the emission frequency of the probe.

The channels 108, 112 are investigated to eliminate false positives. In one embodiment, the investigation includes removing the amount of auto-fluorescence that reaches the second detection channel (e.g, the red channel). For example, some part of the first detection channel (e.g., the green channel) is subtracted from the second channel (e.g., the red channel). Then only the locations where the detected red dye signal is larger than the detected green dye signal will be determined a "positive hit," eliminating signals caused by auto-fluorescence.

Another investigation of the present application includes comparing the two channels. More particularly, when it is determined the signal of the first channel (e.g., green channel) is less than the second channel (e.g., red channel), the entire signal from the signal of the second channel is used to generate a corresponding image. The second embodiment may increase the signal strength used to generate the images.

A more general case would be that a ratio of the values in the channels that identify a separation between auto-fluorescence and labeled cells is empirically determined, and the number of that ratio is used to identify cells of interest.

Figure 5:
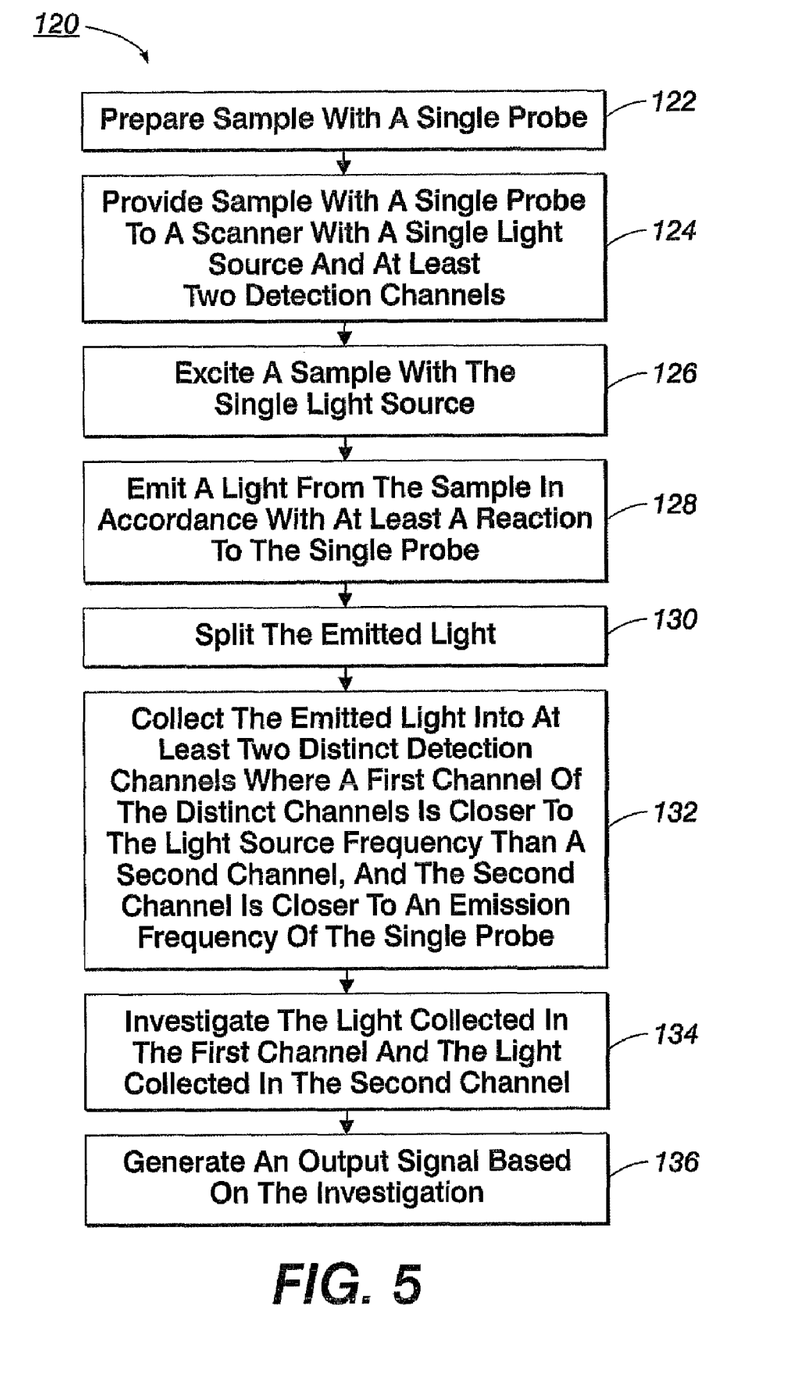
FIG. 5 is a flowchart outlining operations in accordance with the present concepts.

To more particularly discuss the process set forth in connection with FIG. 4, attention is directed to the flow diagram 120 of FIG. 5. In step 122, a sample is prepared with a single probe, and is provided to a scanner system such as the FAST system, where the FAST system is preferably configured with a single light source and at least two detection channels (step 124). Then the single laser source excites the sample (step 126), causing emission of light from the sample in accordance with the reaction to the single probe and auto-fluorescence due to dirt particles, slide imperfections, etc. (step 128). The generated light is then split (step 130) and collected into the at least two distinct input or detection channels (step 132). The first detection channel has been arranged to be closer to the light source frequency, and the second detection channel closer to the emission frequency of the single probe. The collected light in the first channel and the second channel is then investigated (step 134). For example, the light is transmitted along respective first and second light paths of the first and second channels, to respective first and second output/detection areas. These output/detection areas may, in one embodiment, be the photodetectors.

In one embodiment, the investigation includes subtracting the light signal of the first channel from the light signal of the second channel. In another embodiment, the investigating includes comparing the value in each channel. Following the investigation, an output signal is generated (step 138) based on the investigation. More particularly, the remainder of the light signal in the second channel will be determined to represent a "positive hit," and the data related to this signal will be displayed. In another embodiment, i.e., the comparison embodiment, the entire light signal of the second channel is used to display the "positive hit."

Figure 6:
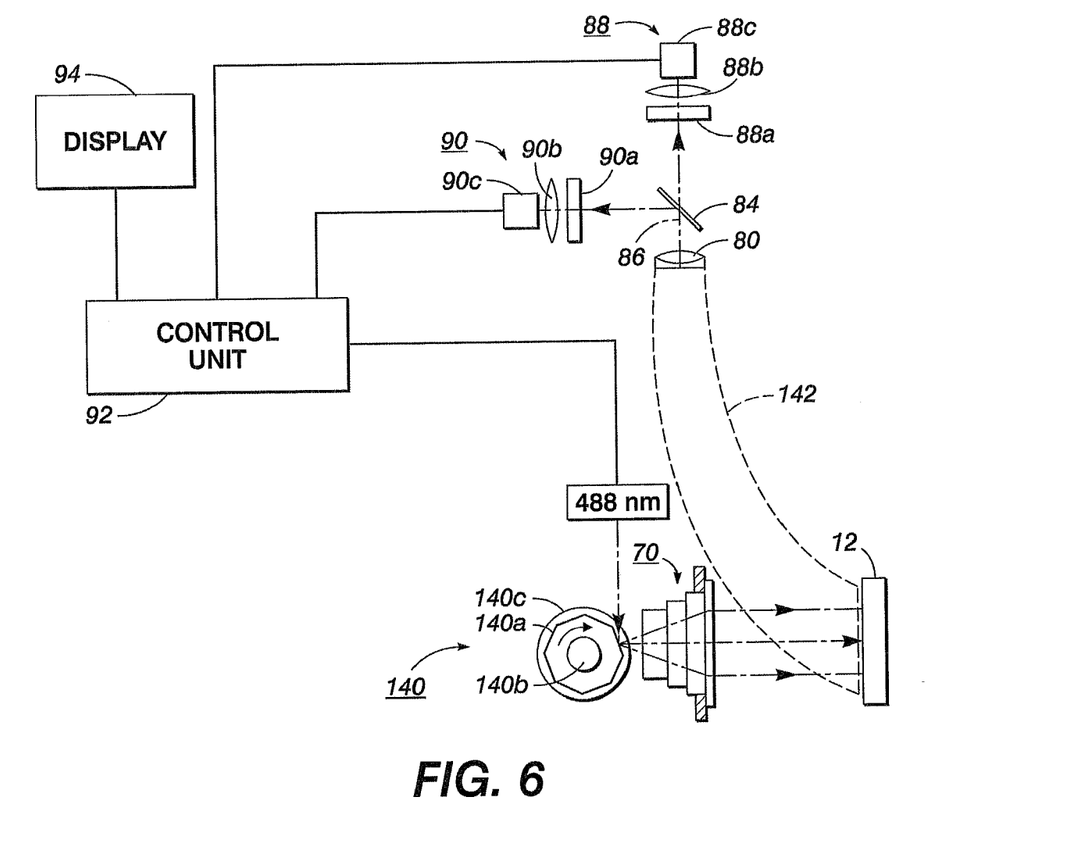
FIG. 6 shows a schematic view of features of a further embodiment.

FIG. 6 depicts a simplified drawing of a system used to facilitate an understanding of another embodiment of the application. Light beam 64 from single laser 62 operating at a single frequency, e.g., 488 nm is provided to a rotating polygon scanner arrangement 140, shown in this exemplary system as a multi-sided mirror 140a, rotated by a motor 140b, and with a flywheel 140c, where the motor and flywheel permit for smooth rotation which eliminates signal jitter. As shown, the described scanner arrangement scans a laser beam through optional lens arrangement 70 to the sample 12.

Stimulated fluorescence from a single probe of sample 12 is received and transmitted along a light path 142 to first lens 80. Focused light beam 82, from light path 142 is split by a dichroic mirror 84, and selective portions of the split light beam are received by first detection channel 88 and second detection channel 90. Each channel is shown with respective blocking filters 88a and 90a, second lens arrangements 88b and 90b, and respective photodetectors 88c and 90c. By this arrangement, one of the photodetectors (e.g., photodetectors 90c) can detect fluorescence from the single probe, as well as auto-fluorescence from both channels, and communicate the detected intensity level as to control unit 92, which will undertake the previously described processing to display or image on display 94.

Although the embodiments have been described with particular reference to cell identification, the described concepts are not limited in application thereto. The imager apparatus configurations shown in the figures are suitable for many imaging applications in which features are to be identified or located. In one such application lying in the biomedical arts, typically ten to ten thousand DNA elements are arranged in an array known in the art as a DNA chip. The DNA elements are processed so that selected elements include a fluorescent tag. The embodiments shown are suitable for identifying the tagged DNA elements in a DNA chip that includes a large number of DNA elements. Implementing the concepts described in the foregoing permits for an imaging apparatus that can access the sample several times faster than existing technology.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A method of identifying auto-fluorescence of a signal comprising:
   applying a single probe to a sample;
   exciting the sample with a single wavelength light source;
   emitting a light from the sample a distance from the light source;
   splitting the emitted light;
   collecting the split light into at least two distinct channels, where a first channel of the distinct channels is closer to the light source frequency than a second channel of the distinct channels, and the second channel is closer to an emission frequency of the single probe than is the first channel;
   investigating the light collected in the first channel and the light collected in the second channel; and
   generating an output signal based on the investigation.

2. The method according to claim 1, wherein the investigating step includes subtracting a value of a light signal of the first channel from a value of a light signal of the second channel to obtain a remainder signal value, wherein when the value of the light signal of the second channel is greater than value of the light signal of the first channel, the remainder signal value of the second channel is used to generate an image.

3. The method according to claim 2, wherein the remainder signal value indicates identification of a rare cell of the sample.

4. The method according to claim 3, wherein the rare cell is one of a cancer cell or a fetal cell.

5. The method according to claim 1, wherein the investigating includes subtracting a value of a light signal of the first channel from a value of a light signal of the second channel to obtain a remainder signal value, wherein when the value of the light signal of the first channel is greater than the value of the light signal of the second channel, the remainder signal value of the signal of the second channel is auto-fluorescence.

6. The method according to claim 2, wherein the remainder signal value indicates a contaminant or particle in the sample.

7. The method according to claim 1, wherein the investigating step includes comparing a value of a light signal in a first channel to a value of a light signal in a second channel and determining the light value in the second channel is a desired signal when the comparing step determines the light value in the second channel is greater than the light value in the first channel.

8. The method according to claim 1, further including:
   empirically determining a ratio between a value of the light signal in the first channel and a value of the light signal in the second channel, wherein the ratio identifies a separation of auto-fluorescence from labeled cells.

9. The method according to claim 1, wherein the first distance of the emitted light is farther out than a Stokes shift of the light source.

10. An imaging method comprising:
    sweeping a single radiation beam along a path on a sample which has had a single probe applied thereto;
    collecting light produced by beam interaction of the single radiation beam with the sample;
    splitting the collected light;
    transmitting the first collected light along a first channel, the first channel channeling the collected light to a selected first output area;
    transmitting the second collected light along a second channel, the second channel channeling the collected light to a selected second output area;
    detecting the first light at the first output area;
    detecting the second light at the second selected output area;
    investigating the first detected light and the second detected light; and
    obtaining an output signal based in the investigating step, wherein the investigating step includes subtracting a value of a light signal of the first channel from a value of a light signal of the second channel to obtain a remainder signal value, and wherein when the value of the light signal of the second channel is greater than value of the light signal of the first channel, the remainder signal value of the second channel is used as the output signal to generate an image.

11. The method according to claim 10, wherein the remainder signal value indicates identification of a rare cell of the sample.

12. The method according to claim 11, wherein the rare cell is one of a cancer cell or a fetal cell.

13. An imaging method comprising:
    sweeping a single radiation beam along a path on a sample which has had a single probe applied thereto;
    collecting light produced by beam interaction of the single radiation beam with the sample;
    splitting the collected light;
    transmitting the first collected light along a first channel, the first channel channeling the collected light to a selected first output area;
    transmitting the second collected light alone a second channel, the second channel channeling the collected light to a selected second output area;
    detecting the first light at the first output area;
    detecting the second light at the second selected output area;
    investigating the first detected light and the second detected light; and
    obtaining an output signal based in the investigating step, wherein the investigating step includes subtracting a value of a light signal of the first channel from a value of a light signal of the second channel to obtain a remainder signal value, and wherein when the value of the light signal of the second channel is greater than value of the light signal of the first channel, the remainder signal value of the second channel is used to generate an image, or wherein the investigating step includes comparing a value of a light signal in the first channel to a value of a light signal in the second channel and determining the light value in the second channel is a desired signal when the comparing step determines the light value in the second channel is greater than the light value in the first channel, the desired signal from the second channel used to generate an image.

14. A scanning imager for imaging a sample having a single probe added thereto, the imager including:
    an imager stage that supports the sample with the single probe;
    a collection light path having a proximate input aperture viewing the sample on the imager stage and a distal output aperture;
    a single scanning radiation source arranged in a fixed relative position to the input aperture to scan a radiation beam on the sample within a viewing area of the input aperture, the radiation beam interacting with the sample to produce light signals that are received by the input aperture and transmitted via the collection light path to the output aperture;

a light splitter positioned to receive and split light from the collection light path;

a first detection channel configured to receive a first portion of the split light;

a second detection channel configured to receive a second portion of the split light;

one of a comparator or subtractor in operative association with the first detection channel and the second detection channel; and a display arranged to display an image based on operation of the comparator or subtractor.

15. The imager as set forth in claim 14, wherein the probe is a fluorescing probe with fluorescence at a single wavelength.

16. The imager as set forth in claim 14, further including, a galvanometer driven mirror.

17. The imager as set forth in claim 14, further including, a rotating polygon scanner having two or more reflective surfaces, each surface arranged to scan radiation from a scanning radiation source over a selected area of the sample.

18. The imager as set forth in claim 14, wherein the detection channels each include a photodetector.

19. The image as set forth in claim 18, when the photodetector is at least one photomultiplier tube.

20. The imager as set forth in claim 18, wherein the scanning radiation source is a light scanner, the imager further including, a light filter arranged to substantially block light produced by the light scanner from reaching the photodetector.

21. The method according to claim 13, the second channel being closer to an emission frequency of the single probe than is the first channel.

* * * * *